(12) United States Patent
Okawauchi et al.

(10) Patent No.: US 7,528,967 B2
(45) Date of Patent: May 5, 2009

(54) OPTICAL CHARACTERISTIC MEASURING APPARATUS AND MEASURING METHOD USING LIGHT REFLECTED FROM OBJECT TO BE MEASURED

(75) Inventors: Makoto Okawauchi, Ritto (JP); Tsutomu Mizuguchi, Ritto (JP); Shiro Kawaguchi, Konan (JP)

(73) Assignee: Otsuka Electronics Co., Ltd., Osaka (JP)

( * ) Notice: Subject to any disclaimer, the term of this patent is extended or adjusted under 35 U.S.C. 154(b) by 0 days.

(21) Appl. No.: 12/121,287

(22) Filed: May 15, 2008

(65) Prior Publication Data
US 2008/0285026 A1    Nov. 20, 2008

(30) Foreign Application Priority Data
May 16, 2007    (JP) .............................. 2007-130372

(51) Int. Cl.
*G01J 3/00* (2006.01)
*G01N 21/55* (2006.01)

(52) U.S. Cl. ...................... 356/622; 356/455; 356/300; 250/372; 250/492.2; 250/559.26

(58) Field of Classification Search ................ 356/601, 356/614, 622, 630, 635, 309–310, 445, 300; 250/559.26, 560, 458.1, 492.2, 237, 341
See application file for complete search history.

(56) References Cited

U.S. PATENT DOCUMENTS

| | | | | |
|---|---|---|---|---|
| 5,101,111 A | * | 3/1992 | Kondo | 250/559.28 |
| 5,120,966 A | * | 6/1992 | Kondo | 250/372 |
| 5,227,861 A | * | 7/1993 | Nishizawa et al. | 356/497 |
| 5,422,703 A | * | 6/1995 | Horie et al. | 356/445 |
| 5,493,401 A | * | 2/1996 | Horie et al. | 356/632 |
| 5,715,061 A | * | 2/1998 | Fujiwara | 356/623 |
| 5,952,668 A | * | 9/1999 | Baer | 250/492.2 |
| 6,142,855 A | * | 11/2000 | Nyui et al. | 451/67 |
| 6,600,560 B2 | * | 7/2003 | Mikkelsen et al. | 356/369 |
| 6,934,025 B2 | * | 8/2005 | Opsal et al. | 356/369 |

FOREIGN PATENT DOCUMENTS

| | | | |
|---|---|---|---|
| JP | 63317706 A | * | 12/1988 |
| JP | 11-230829 | | 8/1999 |
| JP | 2002005823 A | * | 1/2002 |

\* cited by examiner

*Primary Examiner*—Sang Nguyen
(74) *Attorney, Agent, or Firm*—Ditthavong Mori & Steiner, P.C.

(57) ABSTRACT

A measurement-purpose light source generates a measurement light used for measuring an optical characteristic of an object to be measured, and the measurement light includes a component in a wavelength range for measurement of the optical characteristic of the object. An observation-purpose light source generates an observation light used for focusing on the object to be measured and checking a position of measurement. The observation light is selected such that the observation light includes a component that can be reflected from the object to be measured. The measurement light and the observation light are thus applied independently to the object to be measured, through a common objective lens, and accordingly improvement of the precision in measurement of the optical characteristic and facilitation of focusing on the object to be measured are achieved simultaneously.

13 Claims, 11 Drawing Sheets

OPTICAL CHARACTERISTIC MEASURING APPARATUS AND MEASURING METHOD USING LIGHT REFLECTED FROM OBJECT TO BE MEASURED

BACKGROUND OF THE INVENTION

1. Field of the Invention

The present invention relates to an optical characteristic measuring apparatus and a measuring method using the optical characteristic measuring apparatus, and more particularly to a technique of measuring an optical characteristic such as the reflectance of a thin film with a higher precision.

2. Description of the Background Art

A microspectroscope is known as a typical optical characteristic measuring apparatus for measuring optical characteristics (optical constants) such as the reflectance, refractive index, extinction coefficient, and film thickness of a thin film by applying light to the thin film formed on a substrate for example and spectroscopically measuring the light reflected therefrom.

A conventional microspectroscope is configured for example as disclosed in FIG. 1 of Japanese Patent Laying-Open No. 11-230829. The microspectroscope includes an illuminating optical system directing an illuminating light emitted from a light source through a half mirror to a sample to be measured that is set on a table, and an converging optical system bringing the light reflected from the sample to be measured to a diffraction grating and to a monitoring-purpose optical system. The diffraction grating functions as spectroscopic means for splitting an observation light from a measurement region on the sample to be measured, and converges the spectrum on a line sensor. From the spectrum measured with the line sensor, an optical characteristic is calculated. The monitoring-purpose optical system uses a relay lens to form an enlarged image of the sample to be measured, on a two-dimensional CCD camera. The enlarged image of the sample to be measured that is produced by the CCD camera is used for checking the position of measurement and for rough focusing.

As described above, the conventional microspectroscope uses the illuminating light emitted from the light source for both of the purpose of measuring the spectrum and the purpose of focusing.

Usually, in the case where an optical characteristic is to be measured, it is necessary to measure the spectrum in the wavelength range for which the optical characteristic is to be measured. In order to allow a user to adjust, with the eyes, the focus on a sample to be measured, the observation light should include a wavelength range in the visible band. Therefore, it is necessary to employ a light source of the illuminating light that has a relatively wide wavelength band including the wavelength range for what is to be measured as well as the visible band. At the same time, for the focusing purpose, a certain level of brightness as well as a relatively wide observation view should be ensured. Thus, it is also necessary that the illuminating light has a relatively large beam diameter.

Here, in order to measure optical characteristics with a higher precision, it is necessary to use an illuminating light that has a less intensity variation and is stable. However, it is difficult to directly obtain an illuminating light having a wide wavelength band, being stable and having a relatively large beam diameter. Accordingly, a generally employed configuration uses a light source generating an illuminating light of a relatively small beam diameter and an expander expanding the beam diameter of the illuminating light. An expanded beam diameter, however, results in a decreased light intensity (quantity of light) per unit area of the illuminating light.

In other words, while a smaller beam diameter is preferred in terms of further enhancing the precision in measurement of optical characteristics, a larger beam diameter is preferred in terms of focusing. As seen from the above, the conventional microspectroscope potentially involves the requirements that cannot be satisfied concurrently, and the improvement of precision in measurement of optical characteristics has been limited.

SUMMARY OF THE INVENTION

The present invention has been made for solving the problems as described above. An object of the invention is to provide an optical characteristic measuring apparatus and an optical characteristic measuring method with which the precision in measurement of optical characteristics is improved and focusing on an object to be measured is further facilitated.

An optical characteristic measuring apparatus according to an aspect of the present invention includes a measurement-purpose light source, an observation-purpose light source, a condensing optical system, a light injecting portion, a light separating portion, an output portion, and an adjusting mechanism. The measurement-purpose light source generates a measurement light including a component in a wavelength range for measurement of an object to be measured. The observation-purpose light source generates an observation light including a component that can be reflected from the object. The condensing optical system to which the measurement light and the observation light are applied condenses the applied light. The light injecting portion, at a predetermined position on an optical path from the measurement-purpose light source to the condensing optical system, injects the observation light. The light separating portion separates a reflected light generated at the object into a measurement reflected light and an observation reflected light. The output portion outputs at least one of a reflected image obtained from the observation reflected light and a signal according to the reflected image. The adjusting mechanism can change a positional relation between the condensing optical system and the object.

According to the present invention, the measurement-purpose light source generates the measurement light used for measuring an optical characteristic of the object to be measured, and the observation-purpose light source generates the observation light used for focusing on the object to be measured and for checking the position of measurement. Therefore, respective optical parameters of the measurement light and the observation light can be set independently of each other. Accordingly, the beam diameter and/or the wavelength range of the measurement light can be set to a value and/or a range appropriate for measuring the optical characteristic, and the beam diameter and/or the wavelength range of the observation light can be set to a value and/or a range appropriate for observation of the object to be measured.

In this way, the precision in measurement of optical characteristics can be improved and focusing on the object to be measured can be further facilitated.

Preferably, the measurement light at the light injecting portion has a beam diameter smaller than a beam diameter of the observation light at the light injecting portion.

Preferably, the optical characteristic measuring apparatus further includes a spectroscopic measuring portion measuring a spectrum of the measurement reflected light. The light separating portion includes a light reflecting portion disposed on an optical path where the reflected light generated at the object propagates. The light reflecting portion includes an opening having a diameter smaller than a beam diameter of the measurement reflected light, the opening being located at a position corresponding to a light axis of the reflected light generated at the object. The spectroscopic measuring portion is positioned to receive the reflected light having passed through the opening.

Preferably, the condensing optical system includes a convex reflecting mirror and a concave reflecting mirror. The convex reflecting mirror directs to the concave reflecting mirror a light entering a region located at least a predetermined radius from a light axis of the measurement light in a cross section orthogonal to the light axis of the measurement light. The concave reflecting mirror concentrates the light from the convex reflecting mirror on the object.

Preferably, the optical characteristic measuring apparatus further includes a mask portion masking a part of the observation light such that a predetermined observation reference image is projected on the object to be measured.

Preferably, the output portion includes a display showing the reflected image.

Preferably, the observation-purpose light source stops generating the observation light in a period in which measurement is performed using the measurement reflected light.

According to another aspect of the present invention, a method of measuring an optical characteristic of an object to be measured, using an optical characteristic measuring apparatus is provided. The optical characteristic measuring apparatus includes a measurement-purpose light source, an observation-purpose light source, a condensing optical system, a light injecting portion, a light separating portion, and an adjusting mechanism. The measurement-purpose light source generates a measurement light including a component in a wavelength range for measurement of the object. The observation-purpose light source generates an observation light including a component that can be reflected from the object. The condensing optical system to which the measurement light and the observation light are applied condenses the applied light. The light injecting portion, at a predetermined position on an optical path from the measurement-purpose light source to the condensing optical system, injects the observation light. The light separating portion separates a reflected light generated at the object into a measurement reflected light and an observation reflected light. The adjusting mechanism can change a positional relation between the condensing optical system and the object. The method includes the steps of: generating the observation light by the observation-purpose light source; obtaining a reflected image from the observation reflected light separated by the light separating portion; driving the adjusting mechanism based on a state of focusing shown by the reflected image; generating the measurement light by the measurement-purpose light source; and measuring a spectrum of the measurement reflected light separated by the light separating portion.

Preferably, the method further includes the step of stopping generation of the observation light by the observation-purpose light source, when generation of the measurement light is started.

According to the present invention, the precision in measurement of optical characteristics can be improved and focusing on an object to be measured can be further facilitated.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
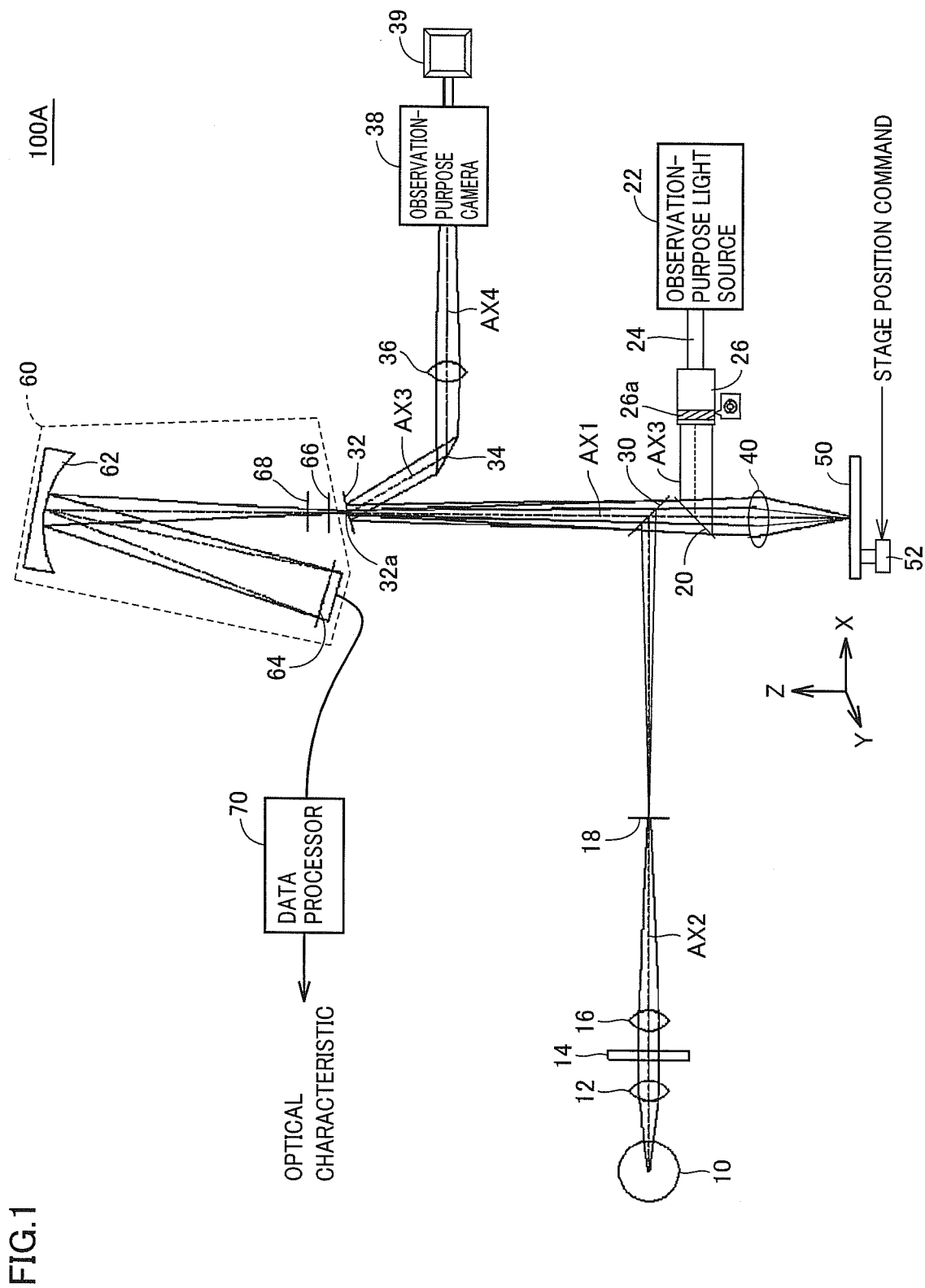
FIG. 1 is a schematic configuration diagram of an optical characteristic measuring apparatus according to a first embodiment of the present invention.

Embodiments of the present invention will be described in detail with reference the drawings. In the drawings, like or corresponding components are denoted by like reference characters and a description thereof will not be repeated.

First Embodiment

An optical characteristic measuring apparatus 100A according to a first embodiment of the present invention is typically a microspectroscopic measuring apparatus, and measures the spectrum of light reflected from an object to be measured (hereinafter also referred to as "object under measurement"), thereby measuring optical characteristics (optical constants) such as (absolute and/or relative) reflectance, refractive index, extinction coefficient, and film thickness of a thin film or the like formed on the object under measurement.

Typical examples of the object under measurement include a device with a thin film formed on any materials such as semiconductor substrate, glass substrate, sapphire substrate, quartz substrate, and film. More specifically, the glass substrate having the thin film formed thereon is used as a display unit of a flat panel display (FPD) such as liquid crystal display (LCD) or plasma display panel (PDP). Further, the sapphire substrate having the thin film formed thereon is used as a nitride semiconductor (GaN: Gallium Nitride)-based LED (Light Emitting Diode) or LD (Laser Diode). Furthermore, the quartz substrate having the thin film formed thereon is used for various optical filters, optical element and projection liquid crystal element for example.

In particular, optical characteristic measuring apparatus 100A in the present embodiment applies a "measurement light" used for measuring optical characteristics of an object under measurement and an "observation light" used for focusing on the object under measurement independently of each other to the object under measurement, so as to simultaneously achieve the improvement of the precision in measurement of optical characteristics and the facilitation of focusing on the object under measurement.

Referring to FIG. 1, optical characteristic measuring apparatus 100A includes a light source 10 used for measurement (hereinafter "measurement-purpose light source"), a collimator lens 12, a cut filter 14, converging lenses 16, 36, a diaphragm 18, beam splitters 20, 30, a tight source 22 used for observation (hereinafter "observation-purpose light source"), an optical fiber 24, an emitting portion 26, a pinhole mirror 32, an axis conversion mirror 34, a camera 38 used for observation (hereinafter "observation-purpose camera"), a display 39, an objective lens 40, a stage 50, a moving mechanism 52, a spectroscopic measuring portion 60, and a data processor 70.

Measurement-purpose light source 10 is a light source generating a measurement light used for measuring optical characteristics of an object under measurement, and is typically a deuterium lamp ($D_2$ lamp) or tungsten lamp or a combination thereof. The measurement light generated by measurement-purpose light source 10 includes a component in a wavelength range for measurement of optical characteristics for the object under measurement (250 nm to 750 nm in the case where the object under measurement is a thin film formed on a glass substrate for example). In particular, in optical characteristic measuring apparatus 100A in the present embodiment, the measurement light is not used for focusing purpose. Therefore, the wavelength range of the measurement light can be set to any range. A measurement light including only the components out of the visible band, such as those in the infrared band or ultraviolet band may be used.

Collimator lens 12, cut filter 14, converging lens 16, and diaphragm 18 are arranged on an optical axis AX2 connecting measurement-purpose light source 10 and beam splitter 30, and optically adjust the measurement light emitted from measurement-purpose light source 10.

Collimator lens 12 is an optical element where the measurement light from measurement-purpose light source 10 first enters, and converts the measurement light propagating in the form of diffused rays into parallel rays by refracting the measurement light. The measurement light having passed through collimator lens 12 enters cut filter 14.

Cut filter 14 is an optical filter for restricting the wavelength range of the measurement light to a wavelength range necessary for measuring optical characteristics. Specifically, since any wavelength component that is included in the measurement light and that is out of the range for measurement could be a factor of a measurement error, cut filter 14 cuts off any wavelength component out of the range for measurement. Typically, cut filter 14 is formed of a multi-layer film vapor-deposited on a glass substrate or the like.

Converging lens 16 converts the measurement light having passed through cut filter 14 from the parallel rays into converging rays, in order to adjust the beam diameter of the measurement light. The measurement light having passed through converging lens 16 enters diaphragm 18.

Diaphragm 18 adjusts the light quantity of the measurement light to an adequate quantity and then applies the light to beam splitter 30. Preferably, diaphragm 18 is disposed at a converging position of the measurement light converted by converging lens 16. The extent to which the quantity of light is adjusted by diaphragm 18 is appropriately set according to the depth of field of the measurement light applied to the object under measurement and the necessary light intensity for example.

In contrast, observation-purpose light source 22 is a light source for generating an observation light used for focusing on the object under measurement as well as for checking the position of measurement. The observation light generated by observation-purpose light source 22 is selected such that the observation light includes a component that can be reflected from the object under measurement. In particular, in optical characteristic measuring apparatus 100A in the present embodiment, the observation light is not used for measuring optical characteristics. Therefore, a light source having a wavelength range and a light quantity appropriate for focusing on the object under measurement and for checking the position of measurement can be employed. Observation-purpose light source 22 is connected through optical fiber 24 to emitting portion 26. The observation light generated by observation-purpose light source 22 propagates through optical fiber 24 which is an optical waveguide and is thereafter emitted from emitting portion 26 toward beam splitter 20.

Emitting portion 26 includes a mask portion 26a masking a part of the observation light generated by observation-purpose light source 22, in order to allow a predetermined observation reference image to be projected on the object under measurement. Specifically, the light intensity (light quantity) at a beam cross section of the observation light immediately after generated by observation-purpose light source 22 is substantially uniform. Mask portion 26a masks (blocks) a part of this observation light, so that the observation light includes a region (shadow region) where the light intensity at a beam cross section is substantially zero. The shadow region is projected as the observation reference image on the object under measurement. The observation reference image is also referred to as reticle image.

Thus, in optical characteristic measuring apparatus 100A in the present embodiment, the observation light including the reticle image is applied to the object under measurement, so that the user can easily adjust the focus based on the projected reticle image, even when an object under measurement has no design (pattern) formed on its surface (the object is typically a transparent glass substrate). Here, the reticle image may be in any shape. For example, a reticle image having a concentric or cross-shaped pattern may be used for example.

Stage 50 is a sample table where the object under measurement is to be disposed, and the surface where the object is disposed is planar-shaped. Stage 50 is driven freely in the three directions (X direction, Y direction, Z direction) by moving mechanism 52 which is mechanically coupled to the stage. Moving mechanism 52 is typically configured to include servo motors for three axes and servo drivers for driving the servo motors respectively. Moving mechanism 52 drives stage 50 in response to a stage position command from a user or a controller (not shown) for example. Stage 50 is thus driven to change the positional relation between the object under measurement and objective lens 40 as described hereinlater.

Objective lens 40, beam splitter 20, beam splitter 30, and pinhole mirror 32 are arranged on an optical axis AX1 extending in the direction perpendicular to the planar surface of stage 50.

Beam splitter 30 reflects the measurement light generated by measurement-purpose light source 10 to convert the direction of propagation of the light to the downward direction, as seen in the drawing, along optical axis AX1. Further, beam splitter 30 passes the light which is reflected from the object under measurement and which propagates upward, as seen in the drawing, along optical axis AX1. Typically, beam splitter 30 is formed of a half mirror.

In contrast, beam splitter 20 reflects the observation light generated by observation-purpose light source 22 to convert the direction of propagation of the light to the downward direction along optical axis AX1 as seen in the drawing. At the same time, beam splitter 20 passes the measurement light reflected from beam splitter 30 and propagating downward along optical axis AX1 as seen in the drawing. Namely, beam splitter 20 functions as a light injecting portion injecting the observation light, at a predetermined position on an optical path from measurement-purpose light source 10 to objective lens 40 that constitutes a condensing optical system. The measurement light and the observation light combined at beam splitter 20 enter objective lens 40. Further, beam splitter 20 passes the light reflected from the object under measurement that propagates upward along optical axis AX1 as seen in the drawing. Typically, beam splitter 20 is formed of a half mirror.

Objective lens 40 constitutes a condensing optical system for concentrating the measurement light and observation light propagating downward along optical axis AX1 as seen in the drawing. Specifically, objective lens 40 converges the measurement light and the observation light so that the light converges at the position of the object under measurement or a position close to the object. Further, objective lens 40 is a magnifier lens having a predetermined magnification (for example ×10, ×20, ×30, ×40). Therefore, a region where optical characteristics of the object under measurement are measured can be made significantly finer as compared with the beam cross section of the light which enters objective lens 40. Thus, optical characteristics of a finer region of the object under measurement can be measured.

The measurement light and the observation light applied from objective lens 40 to the object under measurement are reflected from the object under measurement to propagate upward along optical axis AX1 as seen in the drawing. The reflected light passes through objective lens 40 and thereafter passes further through beam splitters 20 and 30 to reach pinhole mirror 32.

Pinhole mirror 32 functions as a light separating portion separating the reflected light generated at the object under measurement into a reflected light for measurement (hereinafter "measurement reflected light") and a reflected light for observation (hereinafter "observation reflected light"). Specifically, pinhole mirror 32 includes a reflection plane reflecting the reflected light from the object under measurement that propagates upward along optical axis AX1 as seen in the drawing, and an opening (pinhole) 32a is formed having its center where the reflection plane and optical axis AX1 cross each other. Pinhole 32a is formed such that the size of the pinhole is smaller than the beam diameter, at the position of pinhole mirror 32, of the measurement reflected light that is the measurement light from measurement-purpose light source 10 and is reflected by the object under measurement. Further, pinhole 32a is disposed at a position coincident with respective converging positions of the measurement reflected light and the observation reflected light that are respectively the measurement light and the observation light reflected from the object under measurement. This configuration allows a part near optical axis AX1 of the reflected light generated at the object under measured to pass through pinhole 32a and enter spectroscopic measuring portion 60. The remaining part of the reflected light has its direction of propagation converted and accordingly enters axis conversion mirror 34.

Spectroscopic measuring portion 60 measures the spectrum of the measurement reflected light having passed through pinhole mirror 32, and outputs the result of measurement to data processor 70. More specifically, spectroscopic measuring portion 60 includes a diffraction grating 62, a detector 64, a cut filter 66, and a shutter 68.

Cut filter 66, shutter 68 and diffraction grating 62 are arranged on optical axis AX1. Cut filter 66 is an optical filter for limiting wavelength components out of the range for measurement included in the measurement reflected light passing through the pinhole and entering spectroscopic measuring portion 60. In particular, cut filter 66 cuts off any wavelength component out of the range for measurement. Shutter 68 is used for blocking light from entering detector 64 in the case for example where detector 64 is reset. Shutter 68 is typically formed of a mechanical shutter driven by an electromagnetic force.

Diffraction grating 62 separates the applied measurement reflected light into light waves with respective wavelengths and then directs respective light waves to detector 64. Specifically, diffraction grating 62 is a reflective diffraction grating and is configured to reflect diffracted light waves at predetermined wavelength intervals in corresponding directions respectively. When the measurement reflected light is applied to diffraction grating 62 configured as described above, each wavelength component included in the light is reflected in its corresponding direction to enter a corresponding detection region of detector 64. Diffraction grating 62 is typically formed of a flat focus type spherical grating.

Detector 64 outputs an electrical signal according to the light intensity of each wavelength component included in the measurement reflected light separated by diffraction grating 62, in order to measure the spectrum of the measurement reflected light. Detector 64 is typically formed of a photodiode array including detecting elements such as photodiodes arranged in an array or a matrix-arranged CCD (Charged Coupled Device).

Diffraction grating 62 and detector 64 are appropriately designed according to the wavelength range for measurement of optical characteristics and wavelength intervals for measurement for example.

Data processor 70 performs various data processing operations (typically fitting, noise removal) based on the result of measurement (electrical signal) from detector 64, and outputs optical characteristics (optical constants) of the object under measurement such as reflectance, refractive index, extinction coefficient, and film thickness.

In contrast, the observation reflected light that is reflected by pinhole mirror 32 propagates along an optical axis AX3 and enters axis conversion mirror 34. Axis conversion mirror 34 converts the direction in which the observation reflected light propagates, from the direction of optical axis AX3 to the direction of an optical axis AX4. Thus, the observation reflected light propagates along optical axis AX4 and enters observation-purpose camera 38.

Observation-purpose camera 38 is an image producing portion where a reflected image is obtained from the observation reflected light, and is typically formed of a CCD (Charged Coupled Device) or CMOS (Complementary Metal Oxide Semiconductor) sensor for example. Observation-purpose camera 38 typically has its sensitivity to the visible band, and in many cases, has sensitivity characteristics different from those of detector 64 having its sensitivity to a predetermined range for measurement. Observation-purpose camera 38 outputs to display 39 an image signal corresponding to the reflected image produced from the observation reflected light. Display 39 shows the reflected image based on the image signal from observation-purpose camera 38. A user sees the reflected image displayed on display 39 to adjust the focus on the object under measurement or check the position for measurement. Display 39 is typically formed of a liquid crystal display (LCD) for example. Instead of observation-purpose camera 38 and display 39, a finder may be provided that allows a user to directly see the reflected image.

Regarding the correspondence between FIG. 1 and the present invention, measurement-purpose light source 10 corresponds to "measurement-purpose light source," objective lens 40 corresponds to "condensing optical system," observation-purpose light source 22 corresponds to "observation-purpose light source," beam splitter 20 corresponds to "light injecting portion," pinhole mirror 32 corresponds to "light separating portion" and "light reflecting portion," pinhole 32*a* corresponds to "opening," observation-purpose camera 38 corresponds to "output portion," moving mechanism 52 corresponds to "adjusting mechanism," spectroscopic measuring portion 60 corresponds to "spectroscopic measuring portion," mask portion 26*a* corresponds to "mask portion," and display 39 corresponds to "display."

As described above, optical characteristic measuring apparatus 100A in the present embodiment includes measurement-purpose light source 10 generating a measurement light used for measuring optical characteristics of an object under measurement and observation-purpose light source 22 generating an observation light used for focusing on the object under measurement that are provided independently of each other. Therefore, in order to further improve the precision in measurement of optical characteristics and further facilitate focusing on the object to be measured, it is desired that the wavelength range and the beam diameter of the measurement light as well as the wavelength range and the beam diameter of the observation light are optimized in the manner as described below.

In terms of further improving the precision in measurement of optical characteristics, it is desired that the beam diameter of the measurement light applied to the object under measurement is relatively small. This is for the reason that the smaller beam diameter allows the light intensity (light quantity) per unit area to increase and thereby allows the light intensity per unit area of the reflected light from the object under measurement to increase, so that the spectrum can be measured more precisely. While the measurement light propagates, slight reflection occurs at a surface of a lens on the optical path, and/or the measurement reflected light converges at a position displaced from pinhole 32*a*. The light that is undesirable to spectroscopic measuring portion 60 (or undesirable to enter spectroscopic measuring portion 20) is also referred to as internal reflected light and may be a factor of a measurement error. The beam diameter of the propagating measurement light can be made smaller to reduce such internal reflected light entering pinhole 32*a*. For example, if the beam diameter of the measurement light is decreased to one-eighth, the internal reflected light can be reduced to approximately one-sixtyfourth, as simply calculated. Moreover, influences of uneven reflection and irregular reflection can be reduced, so that actually the internal reflected light can be further reduced.

In contrast, in terms of further facilitating focusing on the object under measurement, it is desirable that the beam diameter of the observation light applied to the object under measurement is relatively large. This is for the purpose of keeping an observation field of view as large as possible.

Accordingly, optical characteristic measuring apparatus 100A in the present embodiment is designed such that the beam diameter of the measurement light at beam splitter 20 is smaller than the beam diameter of the observation light at beam splitter 20.

Figure 2:
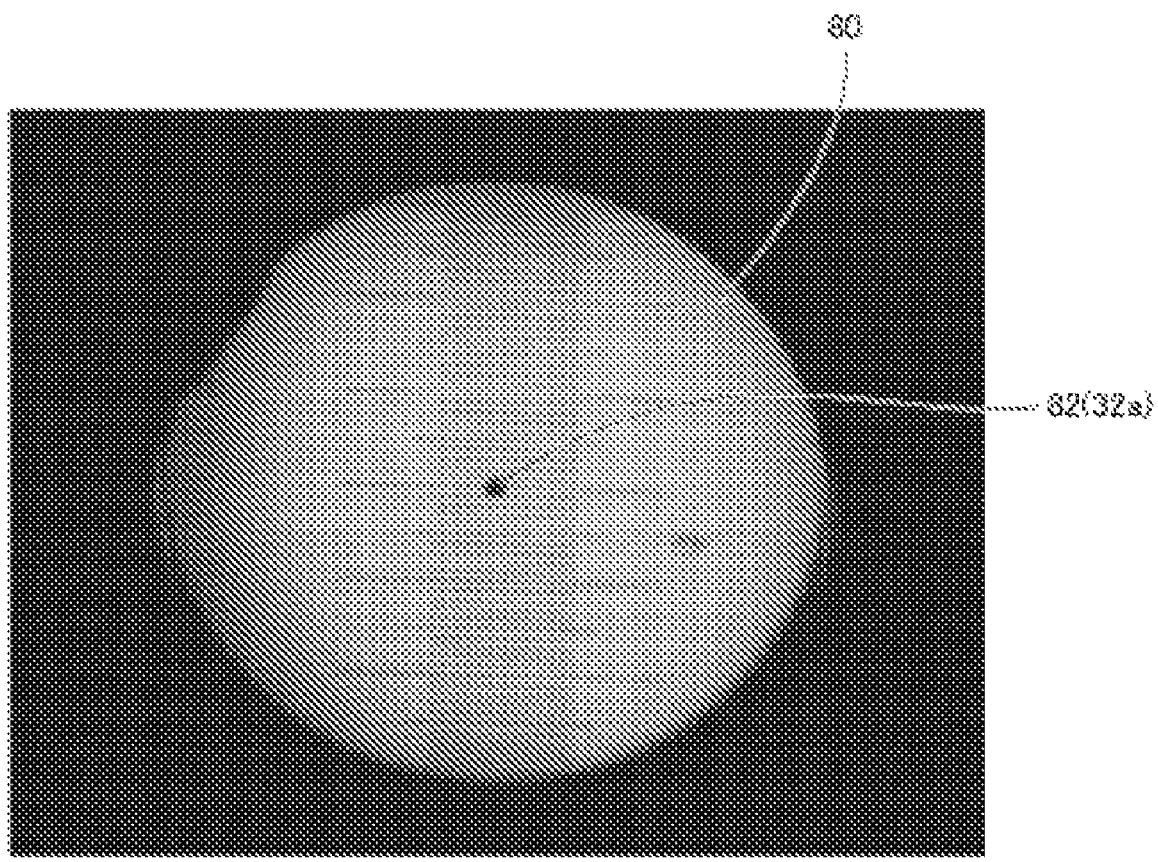
FIG. 2 is a diagram showing an example of a reflected image obtained using an observation-purpose camera.

FIG. 2 is a diagram showing an example of a reflected image obtained using observation-purpose camera 38. FIG. 2 shows the example in the case where the observation light emitted from observation-purpose light source 22 has a beam diameter of 6 mm and objective lens 40 has ×10 (times) magnification.

Referring to FIG. 2, a field of observation 80 ensured by the observation light is approximately 0.6 mm (6 mm ×1/10 (times)). Here, the scale in FIG. 2 is shown for convenience of description. For an actual object under measurement, such a scale is not necessarily required. In a central region of this field of observation 80, a shadow portion 82 is present due to pinhole 32*a* provided in pinhole mirror 32 (FIG. 1). The light corresponding to this shadow portion 82 enters spectroscopic measuring portion 60, as the measurement reflected light.

Further, in terms of further improving the precision in measurement of optical characteristics, it is preferable that the wavelength range of the measurement light is made identical as much as possible to the range for measurement. This is for the reason that any wavelength component out of the range for measurement could cause a measurement error.

In contrast, in terms of further facilitating focusing on the object under measurement, it is desirable to use an observation light including many components in a wavelength range where a relatively high reflectance at the object under measurement is provided. This is for the reason that the state of the object under measurement is visually detected based on the reflected light (namely reflected image) from the object under measurement. In the case where a general object is to be measured, it is sufficient to use an observation light including wavelengths in the visible band. However, in the case where a visible antireflection coating or the like is to be measured, the extremely low reflectance in the visible band hinders a sufficient reflected image from being produced, and accordingly focusing fails. In such a case, the focusing can be achieved by using any observation light having a wavelength out of the visible band (near-infrared light for example) and using a near-infrared camera having its sensitivity to the near-infrared light, as observation-purpose camera 38. Further, in the case where the object under measurement is a very thin object such as film, a difference between the state where the focus is on the front surface and the state where the focus is on the rear surface is small, and it is difficult to distinguish them from each other. Specifically, since the wavelength in the visible band passes through the film, the reflected light at the front surface and the reflected light at the rear surface are mixed with each other. Therefore, it is difficult to determine on which of the surfaces the focus is present. Accordingly, as the observation light, an ultraviolet light which has a low transmittance for the film and which is reflected from only the front surface of the film is used to facilitate focusing on the front surface. In order to make such an ultraviolet light visible, an ultraviolet camera having its sensitivity to the ultraviolet light is used as observation-purpose camera 38.

Further, in terms of further improving the precision in measurement of optical characteristics, it is also desirable to block the observation light from being generated from observation-purpose light source 22 during the measurement by spectroscopic measuring portion 60. Thus, in response to a measurement active signal (not shown) at spectroscopic measuring portion 60, observation-purpose light source 22 may stop generating the observation light.

Figure 3A:
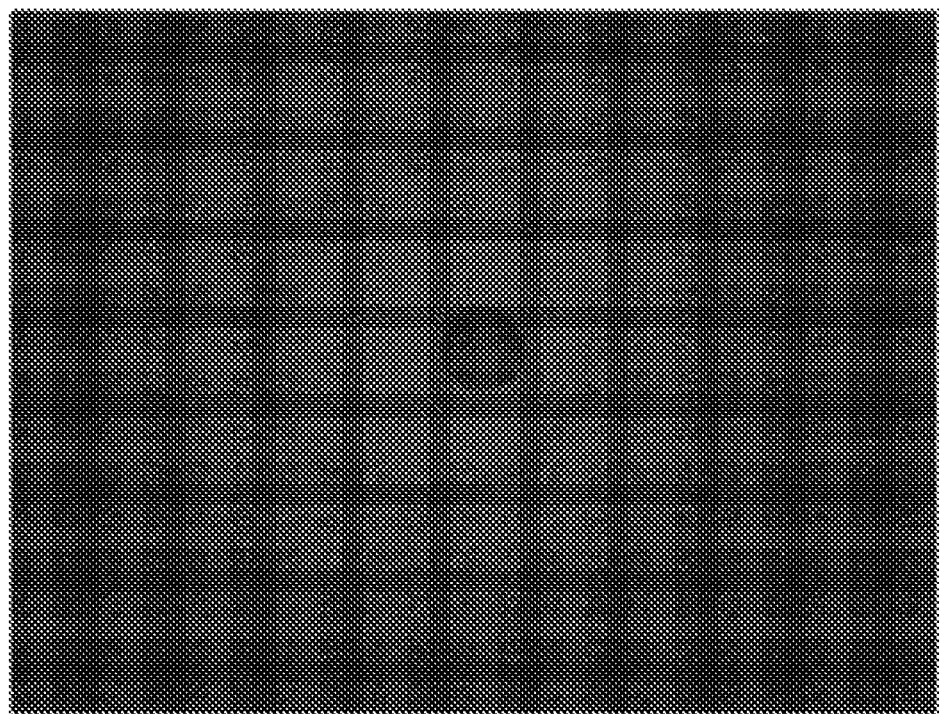
FIGS. 3A and 3B are each a diagram showing an example of a reflected image obtained using the observation-purpose camera in the case where a visible antireflection coating is used as an object to be measured.
Figure 3B:
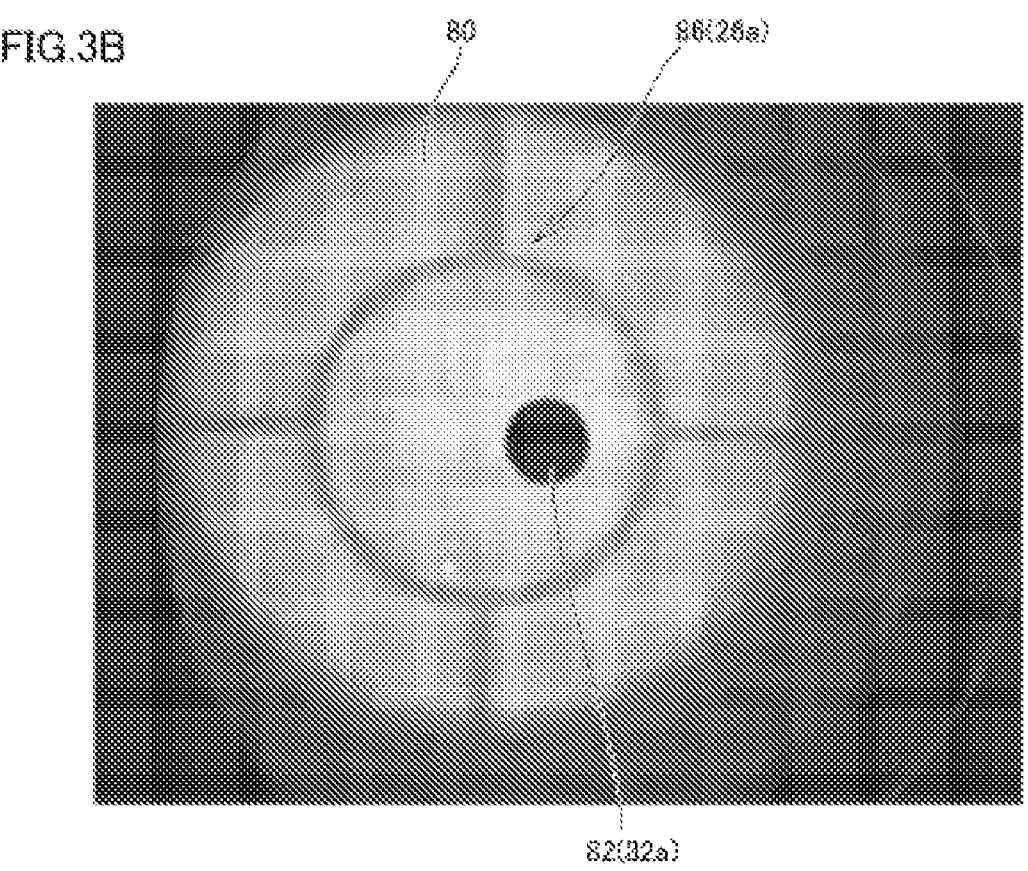

FIGS. 3A and 3B are diagrams each showing an example of the reflected image obtained using observation-purpose camera 38 in the case where a visible antireflection coating is used as the object to be measured. FIG. 3A shows an example where the observation light as used is a light having wavelengths in the visible band, and FIG. 3B shows an example where the observation light as used is a light having near-infrared wavelengths.

As shown in FIG. 3A, since the visible antireflection coating has an extremely low reflectance for the wavelengths in the visible band, a visually detectable reflected image cannot be obtained even if an observation light having a wavelength in the visible band is used. In contrast, as shown in FIG. 3B, since the visible antireflection coating has a significant degree of reflectance for the near-infrared wavelengths, visually detectable field of observation 80 can be obtained by using an observation light having the near-infrared wavelengths. Here, in a central region of this field of observation 80, a shadow portion 82 generated due to pinhole 32a provided in pinhole mirror 32 (FIG. 1) is present. Further, a reticle image (reference image for observation) 86 is projected that is generated at mask portion 26a (FIG. 1). Therefore, a user can adjust the focus with reference to this reticle image.

In the following, with reference to the flowchart shown in FIG. 4, a description will be given of a procedure for measuring an optical characteristic of an object under measurement, using optical characteristic measuring apparatus 100A in the present embodiment.

Figure 4:
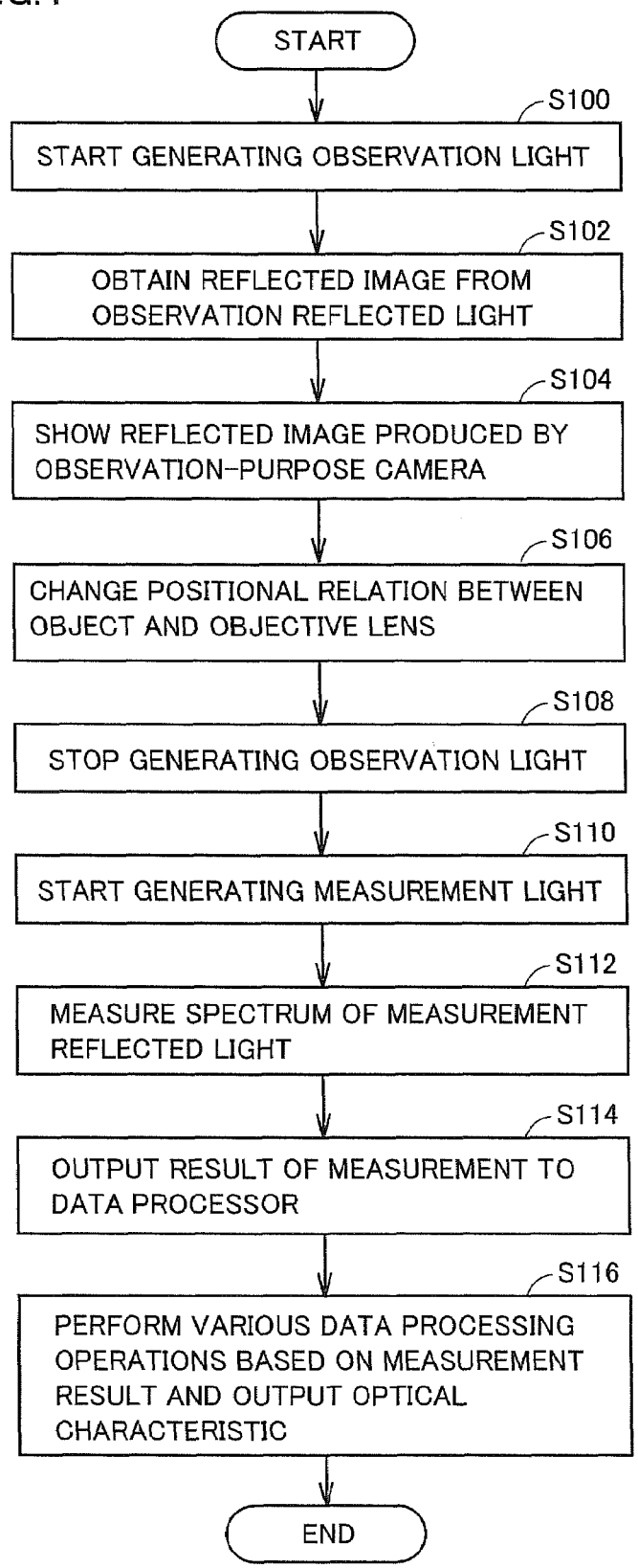
FIG. 4 is a flowchart showing a procedure for measuring an optical characteristic of an object to be measured, using the optical characteristic measuring apparatus according to the first embodiment of the present invention.

FIG. 4 is a flowchart showing a procedure for measuring an optical characteristic of an object to be measured, using optical characteristic measuring apparatus 100A in the first embodiment of the present invention.

Referring to FIG. 4, in response to operation by a user for example, observation-purpose light source 22 starts generating an observation light (step S100). The generated observation light is applied to the object under measurement through objective lens 40. Then, the observation reflected light generated at the object under measurement enters observation camera 38 through pinhole mirror 32 and so on. Observation-purpose camera 38 obtains a reflected image from this observation reflected light (step S102), and display 39 shows the reflected image produced by observation-purpose camera 38 (step S104).

While seeing the state of focusing of the reflected image shown by display 39, the user gives a stage position command to moving mechanism 52 to change the positional relation between the object under measurement (stage 50) and objective lens 40 (step S106).

After focusing is completed, the user gives a command to start optical measurement. In response to the command, observation-purpose light source 22 stops generating the observation light (step S108) and measurement-purpose light source 10 starts generating a measurement light (step S110). The generated measurement light is applied to the object under measurement through objective lens 40. Then, the measurement reflected light generated at the object under measurement passes through pinhole 32a of pinhole mirror 32 and enters spectroscopic measuring portion 60. Spectroscopic measuring portion 60 measures the spectrum of the measurement reflected light (step S112), and outputs the result of measurement to data processor 70 (step S114). Based on the measurement result from detector 64, data processor 70 performs various data processing operations, and outputs an optical characteristic such as the reflectance, refractive index, extinction coefficient or film thickness of the object under measurement (step S116).

Through the series of steps as described above, the optical characteristic of the object under measurement can be measured.

Although the description above concerns the configuration where the positional relation between the object under measurement and objective lens 40 is changed by the user with reference to the state of focusing of the reflected image shown by display 39, a controller (not shown) may perform focusing a known automatic focusing technique.

According to the first embodiment of the present invention, the measurement-purpose light source generates the measurement light used for measuring optical characteristics of an object under measurement, while the observation-purpose light source generates the observation light used for focusing on the object under measurement and checking the position of measurement. Therefore, respective optical parameters of the measurement light and the observation light can be set independently of each other. Thus, the beam diameter and/or the wavelength range of the measurement light can be set to a value and/or a range appropriate for measuring optical characteristics. Further, the beam diameter and/or the wavelength range of the observation light can be set to a value and/or a range appropriate for observation of the object under measurement.

Accordingly, both of the improvement of the precision in measurement of optical characteristics and the further facilitation of focusing on the object under measurement can be achieved at the same time.

Further, according to the first embodiment of the present invention, the beam diameter of the measurement light can be set to any diameter. Therefore, the beam diameter can be made relatively small to reduce a measurement error due to an internally reflected light generated at a lens surface for example. In this way, the precision in measurement can be improved and optical characteristics of a very small region of the object under measurement can be measured.

Furthermore, according to the first embodiment of the present invention, the wavelength range of the observation light can be set to any range. Therefore, the observation light including a wavelength with a relatively high reflectance at the object under measurement can be used to facilitate focusing on an object such as a visible antireflection coating or film for which the focusing by a light having a wavelength in the visible band is difficult.

Second Embodiment

Regarding optical characteristic measuring apparatus 100A in the first embodiment of the present invention, the configuration using the refractive lens as the objective lens is described as an example. Depending on the type of the object under measurement, however, a reflected light from the rear surface of the object under measurement could appear as a stray light to deteriorate the precision in measurement, despite the fact that the focus is adjusted on the front surface of the object under measurement. In such a case, preferably a reflective objective lens as described below is used.

Figure 5:
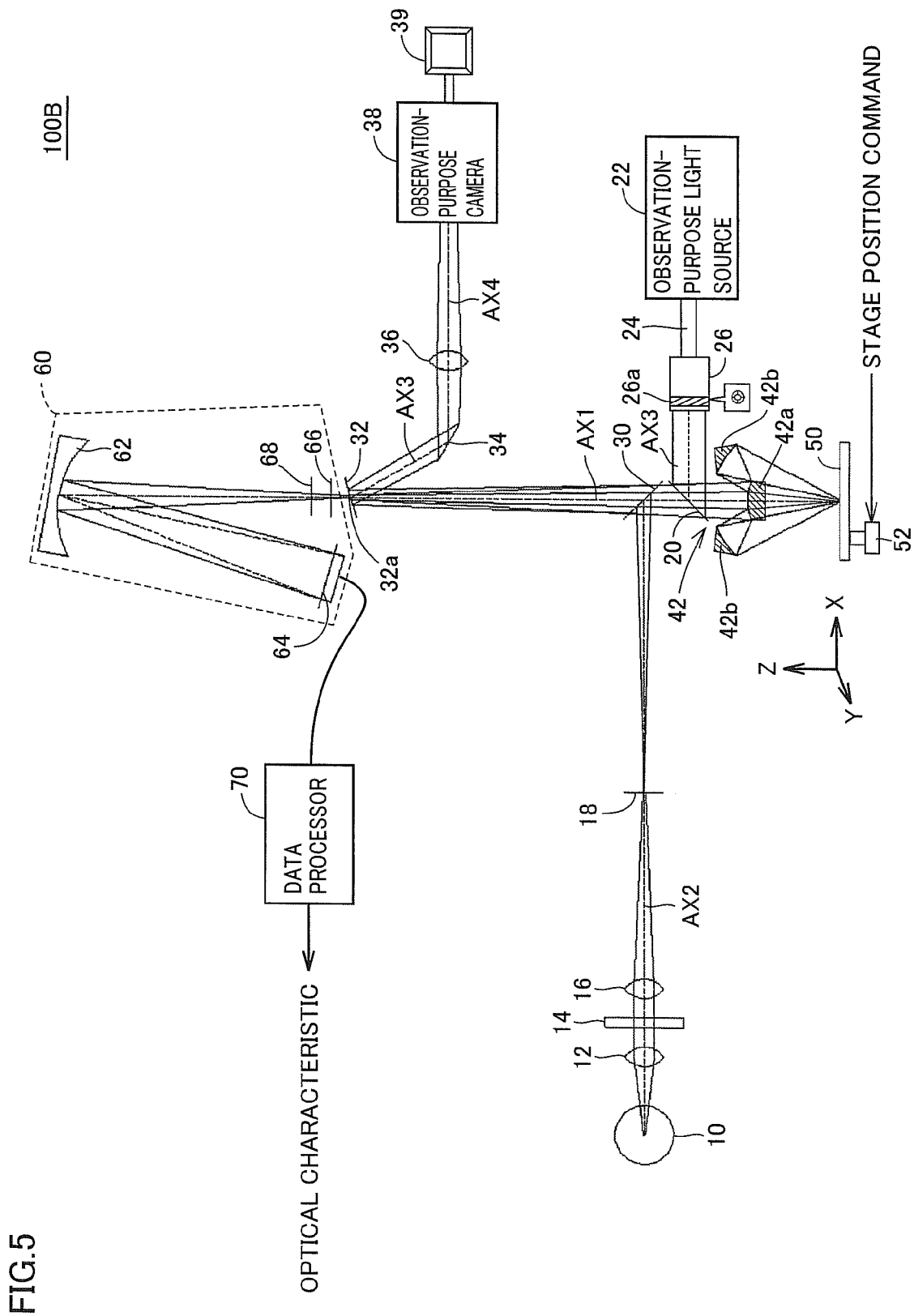
FIG. 5 is a schematic configuration diagram of an optical characteristic measuring apparatus according to a second embodiment of the present invention.

FIG. 5 is a schematic configuration diagram of an optical characteristic measuring apparatus 100B according to a second embodiment of the present invention.

Referring to FIG. 5, optical characteristic measuring apparatus 100B in the second embodiment of the present invention differs from optical characteristic measuring apparatus 100A shown in FIG. 1 in that a reflective objective lens 42 is employed instead of objective lens 40. Other components are similar to those of optical characteristic measuring apparatus 100A shown in FIG. 1, and the detailed description will not be repeated.

Reflective objective lens 42 is typically a Cassegrain-type reflective objective lens. Specifically, reflective objective lens 42 includes a convex reflecting mirror 42a and a concave reflecting mirror 42b in combination.

Convex reflecting mirror 42a and concave reflecting mirror 42b are arranged such that their central axes and optical axis AX1 coincide with each other. Convex reflecting mirror 42a reflects a part of the observation light and the measurement light propagating on optical axis AX1 and directs the reflected light to concave reflecting mirror 42b. Concave reflecting mirror 42b is a concentric mirror. In FIG. 5, a cross-sectional shape of concave reflecting mirror 42b is schematically shown. Concave reflecting mirror 42b concentrates a part of the observation light and the measurement light reflected from convex reflecting mirror 42a on the object under measurement. The reflected light from the object under measurement propagates through the same optical path as the incident path in the opposite direction.

Figure 6:
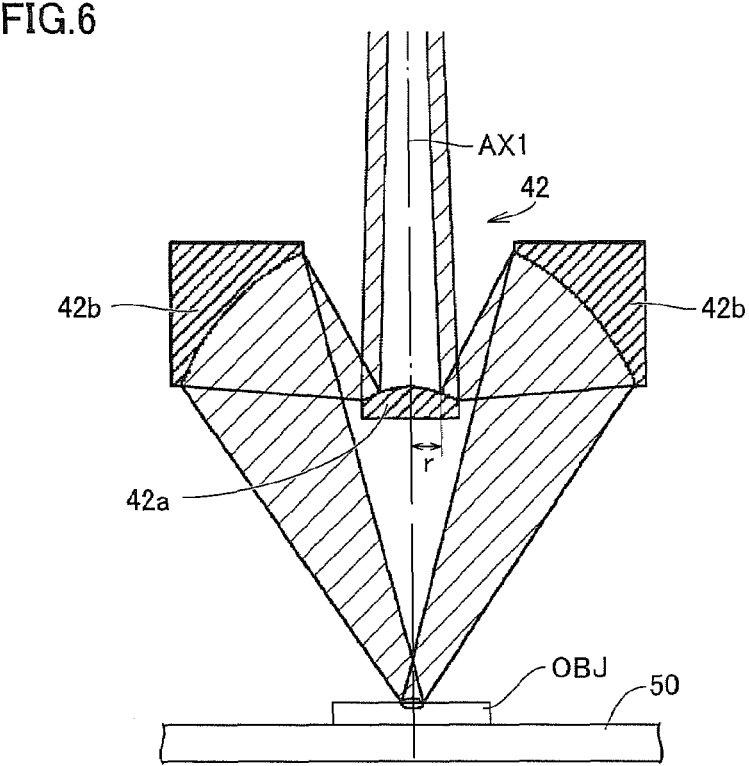
FIG. 6 is a detailed configuration diagram of a reflective objective lens according to the second embodiment of the present invention.

FIG. 6 is a more detailed configuration diagram of reflective objective lens 42 in the second embodiment of the present invention.

Referring to FIG. 6, convex reflecting mirror 42a directs to concave reflecting mirror 42b only the light portion corresponding to a region at a predetermined radius r or more from optical axis AX1 in a cross section orthogonal to optical axis AX1, of the light (measurement light and observation light) applied along optical axis AX1. In contrast, the light portion corresponding to a region at less than predetermined radius r from optical axis AX1, namely the region near optical axis AX1, is reflected by convex reflecting mirror 42a so as not to be directed to concave reflecting mirror 42b. In other words, only the measurement light and the observation light applied to a region at at least predetermined radius r from optical axis AX1 of convex reflecting mirror 42a is applied to object under measurement OBJ. Therefore, a cross section of the light beam before incident on object under measurement OBJ is concentric (doughnut-shaped) having its central region which is masked. The light having the concentric cross section of the beam can be used to avoid the influence of the rear-surface reflected light (stray light) that is generated by being reflected from the rear surface of object under measurement OBJ.

Figure 7:
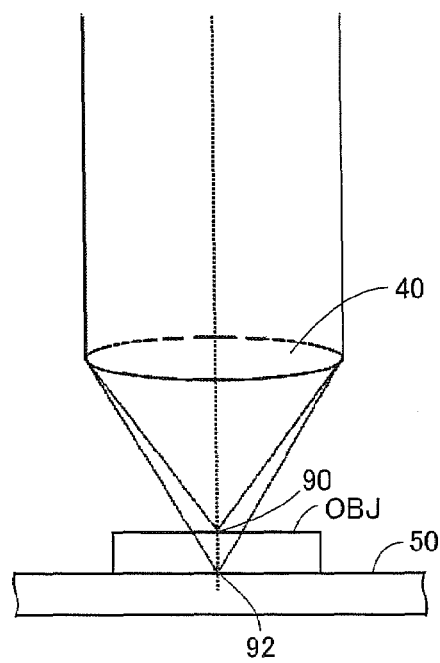
FIG. 7 is a conceptual diagram illustrating a state in which a rear-surface reflected light is generated in the case where a refractive objective lens is used.

FIG. 7 is a conceptual diagram illustrating a state in which the rear-surface reflected light is generated in the case where a refractive objective lens is used.

Referring to FIG. 7, particularly in the case where the film thickness of an object under measurement OBJ is relatively small, due to the lens aberration or the like of refractive objective lens 40, a reflected light could be generated at both of the interfaces on a front surface 90 and a rear surface 92 of object under measurement OBJ. Namely, despite of the fact that only the reflected light from front surface 90 of object under measurement OBJ is necessary, the reflected light from rear surface 92 acts as a stray light mixed therewith. The reflected light from rear surface 92 is a factor of a measurement error.

Figure 8A:
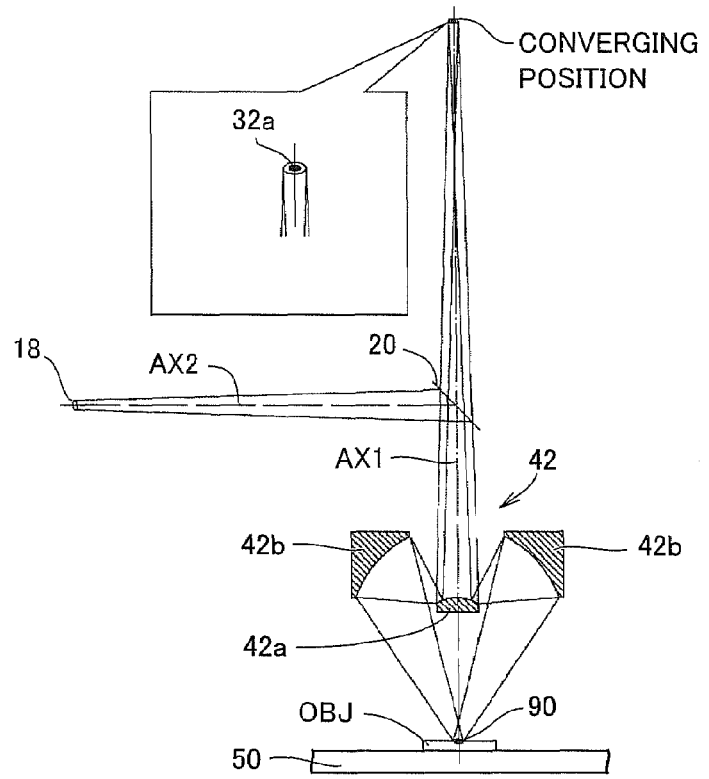
FIGS. 8A and 8B are each a conceptual diagram illustrating a state in which a rear-surface reflected light is generated in the case where a reflective objective lens is used.
Figure 8B:
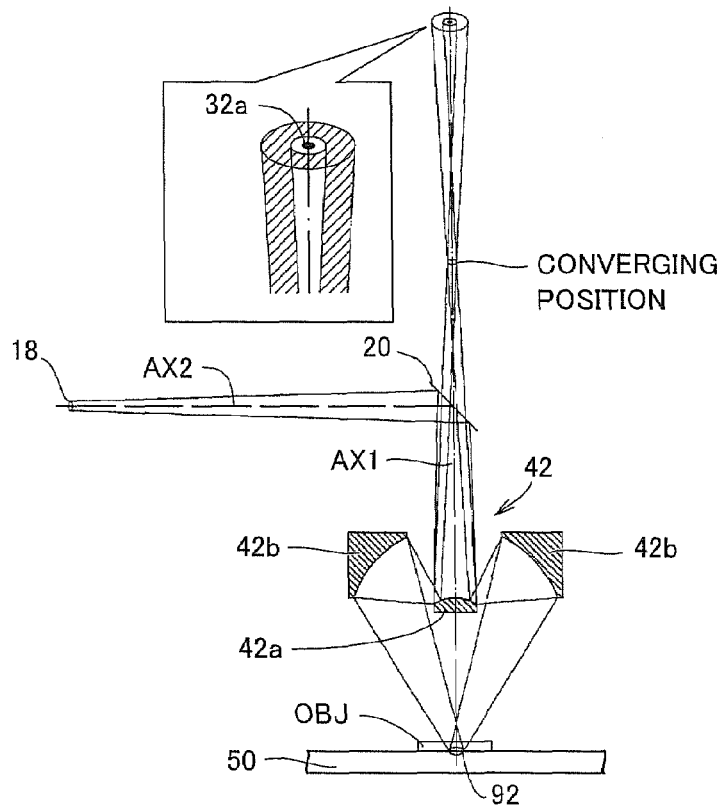

Referring next to FIGS. 8A and 8B, a description will be given of a reason why the influence of the reflected light from rear surface 92 can be avoided by using reflective objective lens 42.

FIGS. 8A and 8B are each a conceptual diagram illustrating a state in which a rear-surface reflected light is generated in the case where the reflective objective lens is used. FIG. 8A shows a reflected light from front surface 90 of object under measurement OBJ, and FIG. 8B shows a reflected light from rear surface 92 of object under measurement OBJ.

In the case where the focus of reflective objective lens 42 is adjusted on front surface 90 of object under measurement OBJ, the measurement reflected light generated by reflection from front surface 90 of object under measurement OBJ propagates along optical axis AX1 through reflective objective lens 42 upward as seen in the drawing. As shown in FIG. 8A, the converging position of the measurement reflected light is designed such that the converging position substantially coincides with the position of pinhole 32a of pinhole mirror 32 (FIG. 5). Thus, the measurement reflected light with the beam diameter narrowed reaches pinhole mirror 32. Therefore, the measurement reflected light passes through pinhole 32a and enters spectroscopic measuring portion 60 (FIG. 5). In the case where the converging position and the position of pinhole 32a are substantially coincident with each other as described above, the light does not have a beam cross section which is concentric at pinhole 32a. Namely, the light keeping its sufficient intensity enters spectroscopic measuring portion 60.

In contrast, as shown in FIG. 8B, the converging portion of the rear-surface reflected light which is generated by reflection from rear surface 92 of object under measurement OBJ is shifted toward reflective objective lens 42 as compared with the converging position of the measurement reflected light shown in FIG. 8A. In the optical path from the converging position to pinhole 32a, the rear-surface reflected light is a doughnut-shaped beam and thus the beam diameter becomes larger as approaching pinhole 32a. When a region without the beam intensity of the rear-surface reflected light (inner region of the beam cross section) is larger than the diameter of pinhole 32a, the rear-surface reflected light cannot pass through pinhole 32a. Namely, the influence of a measurement error due to the rear-surface reflected light can be avoided if the optical difference as described above can be achieved.

Accordingly, optical characteristic measuring apparatus 100B in the present embodiment appropriately sets the size and so on of reflective objective lens 42 according to the film thickness and so on of object under measurement OBJ, so that an optical difference as shown in FIGS. 8A and 8B is provided between the reflected light from the front surface and the reflected light from the rear surface.

As shown in FIGS. 8A and 8B, it is important to appropriately set the beam diameter of the measurement light, for avoiding the influence of the rear-surface reflected light. The influence of the beam diameter of the measurement light will be described with reference to FIGS. 9A and 9B.

Figure 9A:
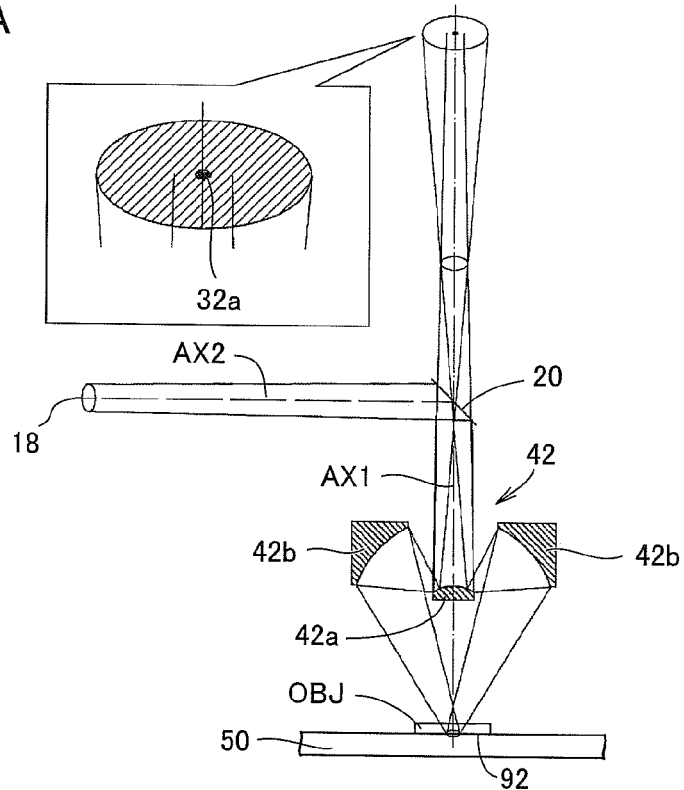
FIGS. 9A and 9B are each a conceptual diagram illustrating the difference in influence of a rear-surface reflected light according to the beam diameter of a measurement light.
Figure 9B:
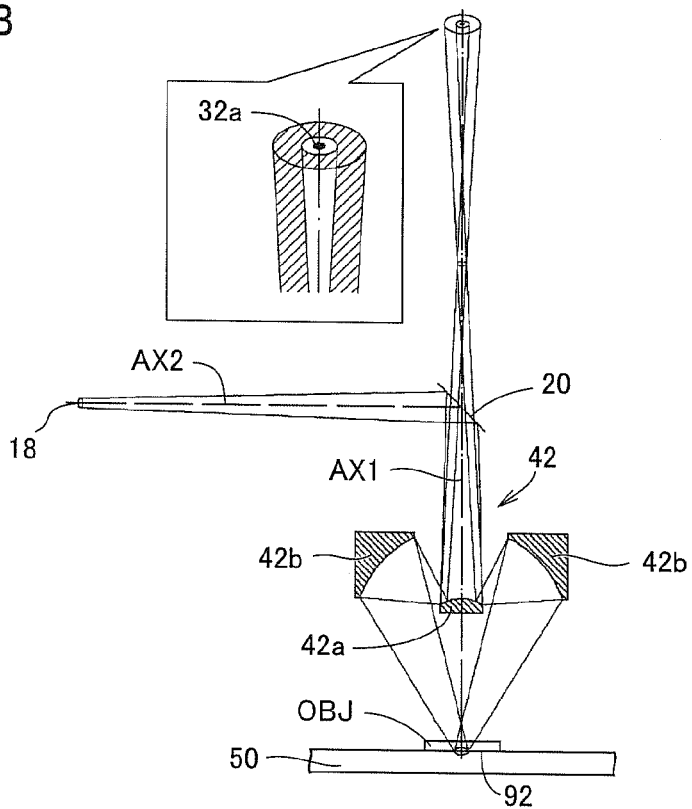

FIGS. 9A and 9B are each a conceptual diagram illustrating the difference in influence of the rear-surface reflected light according to the beam diameter of the measurement light. FIG. 9A shows that the beam diameter of the measurement light is made relatively large, and FIG. 9B shows that the beam diameter of the measurement light is made relatively small.

As shown in FIG. 9A, the measurement light is applied to reflective objective lens 42 without its beam diameter sufficiently reduced. Then, the beam cross section itself of the rear-surface reflected light generated by being reflected from rear surface 92 of object under measurement OBJ is large. Accordingly, the beam intensity at the position of pinhole 32a does not have a masked portion. Specifically, the beam intensity of the rear-surface reflected light at the position of pinhole 32a is not doughnut-shaped but circular-shaped, and a part of the light passes through pinhole 32a and enters spectroscopic measuring portion 60. As a result, the influence of the rear-surface reflected light cannot be avoided sufficiently. Therefore, it is desirable as shown in FIG. 9B that the measurement light with its beam diameter appropriately reduced by diaphragm 18 is applied to reflective objective lens 42.

Example of Measurement Results

Figure 10:
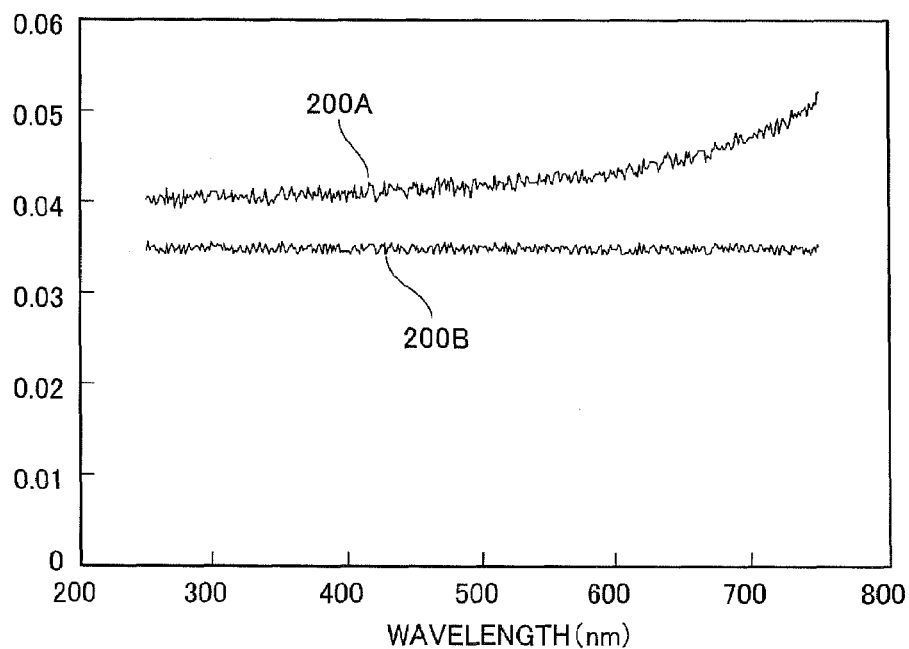
FIG. 10 is a diagram showing the result of measurement of the reflectance of an object to be measured, obtained by using the optical characteristic measuring apparatus according to the second embodiment of the present invention, and the result thereof obtained by using a conventional optical characteristic measuring apparatus, as compared with each other.

FIG. 10 is a diagram showing the result of measurement of the reflectance of an object under measurement obtained by using optical characteristic measuring apparatus 100B in the second embodiment of the present invention, as well as the result thereof obtained by using a conventional optical characteristic measuring apparatus, as compared with each other. Regarding FIG. 10, the object under measurement is a silicon oxide thin film on a glass that is a low-reflectance sample employed as an antireflection coating for practical use, and the result of measurement of the reflectance spectrum of the object under measurement is shown. In FIG. 10, a measurement result 200A represents data obtained by using a conventional optical characteristic measuring apparatus that generates the measurement light and the observation light by a common light source as shown in FIG. 1 of Japanese Patent Laying-Open No. 11-230829. A measurement result 200B represents data obtained by using optical characteristic measuring apparatus 100B in the present embodiment.

Measurement result 200A of the conventional optical characteristic measuring apparatus is approximately 1.5 times as large as measurement result 200B. A reason for this is considered as follows. In the conventional optical characteristic measuring apparatus, the measurement reflected light and the observation reflected light cannot be separated sufficiently from each other. Therefore, a part of the observation reflected light acts as a stray light and enters spectroscopic measuring portion 60, resulting in a measurement error. The difference between the measurement results is more noticeable for a low-reflectance sample like this object under measurement.

Figure 11:
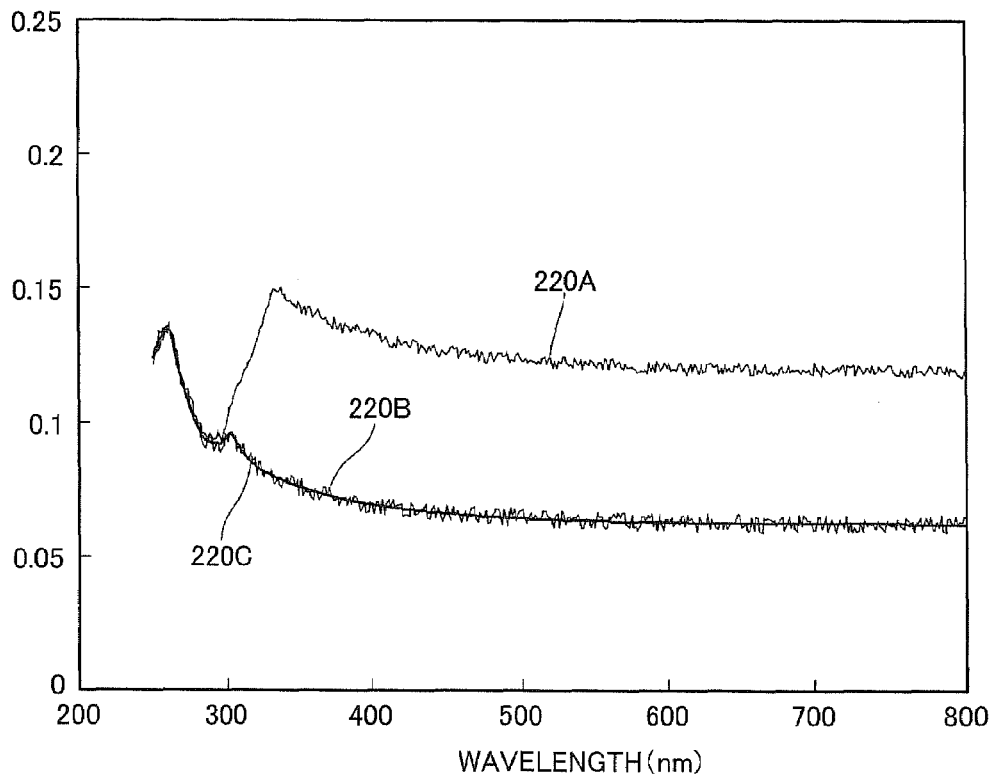
FIG. 11 is a diagram showing the result of measurement of the reflectance of an object to be measured, obtained by using the optical characteristic measuring apparatus according to the second embodiment of the present invention, and the result thereof obtained by using a conventional optical characteristic measuring apparatus, as compared with each other.

FIG. 11 is a diagram showing the result of measurement of the reflectance of an object under measurement obtained by using optical characteristic measuring apparatus 100B in the second embodiment of the invention, as well as the result thereof obtained by using a conventional optical characteristic measuring apparatus, as compared with each other. FIG. 11 shows the result of measuring the reflectance spectrum of a PET film having a thickness of 0.2 mm used as an object under measurement. In FIG. 11, a measurement result 220A represents data obtained by using the conventional optical characteristic measuring apparatus, and a measurement result 220B represents data obtained by using optical characteristic measuring apparatus 100B in the present embodiment. A theoretical value 220C represents a calculated theoretical value of the reflectance spectrum from only the front surface of the PET film as calculated from known refractive index and extinction coefficient of the PET film (object under measurement).

Referring to FIG. 11, it is seen that measurement result 220A of the conventional optical characteristic measuring apparatus is approximately twice as large as theoretical value 220C. This is for the reason that the rear-surface reflected light is mixed with the front-surface reflected light of the PET film. In contrast, it is seen that measurement result 220B is well coincident with theoretical value 220C. In other words, what is meant here is that optical characteristic measuring apparatus 100B in the present embodiment can measure an optical characteristic of an object under measurement with a higher precision while avoiding the influence of the rear-surface reflected light, even in the case where the object under measurement has a relatively thin thickness such as approximately 0.2 mm.

According to the second embodiment of the present invention, the effect that the influence of the rear-surface reflected light can be avoided can be achieved in addition to the effect obtained in the first embodiment as described above. Specifically, since reflective objective lens 42 is used to prevent the rear-surface reflected light generated by being reflected from the rear surface of the object under measurement from entering spectroscopic measuring portion 60, a measurement error due to the rear-surface reflected light can be reduced. Therefore, optical characteristics can be measured with a higher precision even for an object under measurement having a relatively thin thickness which is likely to cause the influence of the rear-surface reflected light.

Third Embodiment

Regarding the optical characteristic measuring apparatus in the first or second embodiment of the invention as described above, the configuration is explained where beam splitter 20 is disposed on the propagation path of the reflected light (measurement reflected light and observation reflected light) to inject the observation light. The position where the observation light is injected, however, is any position as long as the position is present on an optical path from measurement-purpose light source 10 to objective lens 40 which constitutes a condensing optical system. Accordingly, regarding a third embodiment of the present invention, a description will be given of a configuration where an observation light is injected on an optical path from measurement-purpose light source 10 to beam splitter 30.

Figure 12:
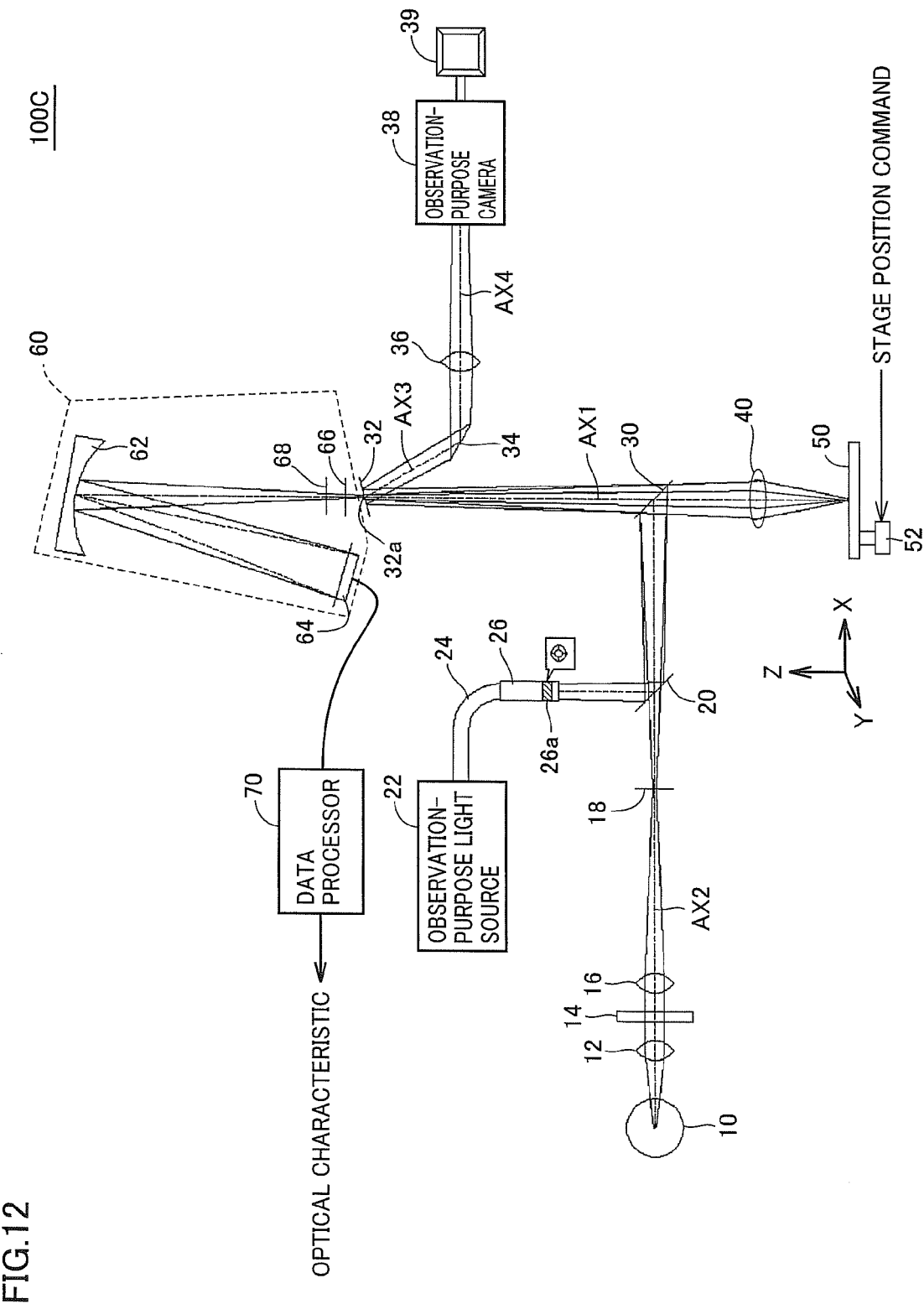
FIG. 12 is a schematic configuration diagram of an optical characteristic measuring apparatus according to a third embodiment of the present invention.

FIG. 12 is a schematic configuration diagram of an optical characteristic measuring apparatus 100C in the third embodiment of the present invention.

Referring to FIG. 12, optical characteristic measuring apparatus 100C in the third embodiment of the present invention differs from optical characteristic measuring apparatus 100A shown in FIG. 1 in that the position of beam splitter 20 is changed to a position on an optical path from measurement-purpose light source 10 to beam splitter 30, and respective positions of observation-purpose light source 22, optical fiber 24 and emitting portion 26 are changed according to the positional change of the beam splitter. Other functions and elements are similar to those of optical characteristic measuring apparatus 100A shown in FIG. 1, and the detailed description thereof will not be repeated.

Optical characteristic measuring apparatus 100C in the present embodiment allows a reflected light (measurement reflected light and observation reflected light) from an object under measurement to pass through only one beam splitter 30. Beam splitter 30 is typically formed of a half mirror. A theoretical transmittance of the half mirror is 50% as the name indicates. Therefore, the light intensity of the light after passing through the half mirror is half (50%) that of the light intensity before passing therethrough. Therefore, the number of beam splitters through which the reflected light passes can be decreased to reduce the amount of attenuation of the reflected light entering spectroscopic measuring portion 60. Therefore, the SN (Signal to Noise) ratio of the spectrum detected by spectroscopic measuring portion 60 can be kept higher.

According to the third embodiment of the present invention, the effect that the precision in measurement can be further improved is obtained in addition to the effect obtained by the above-described first embodiment.

Fourth Embodiment

Figure 13:
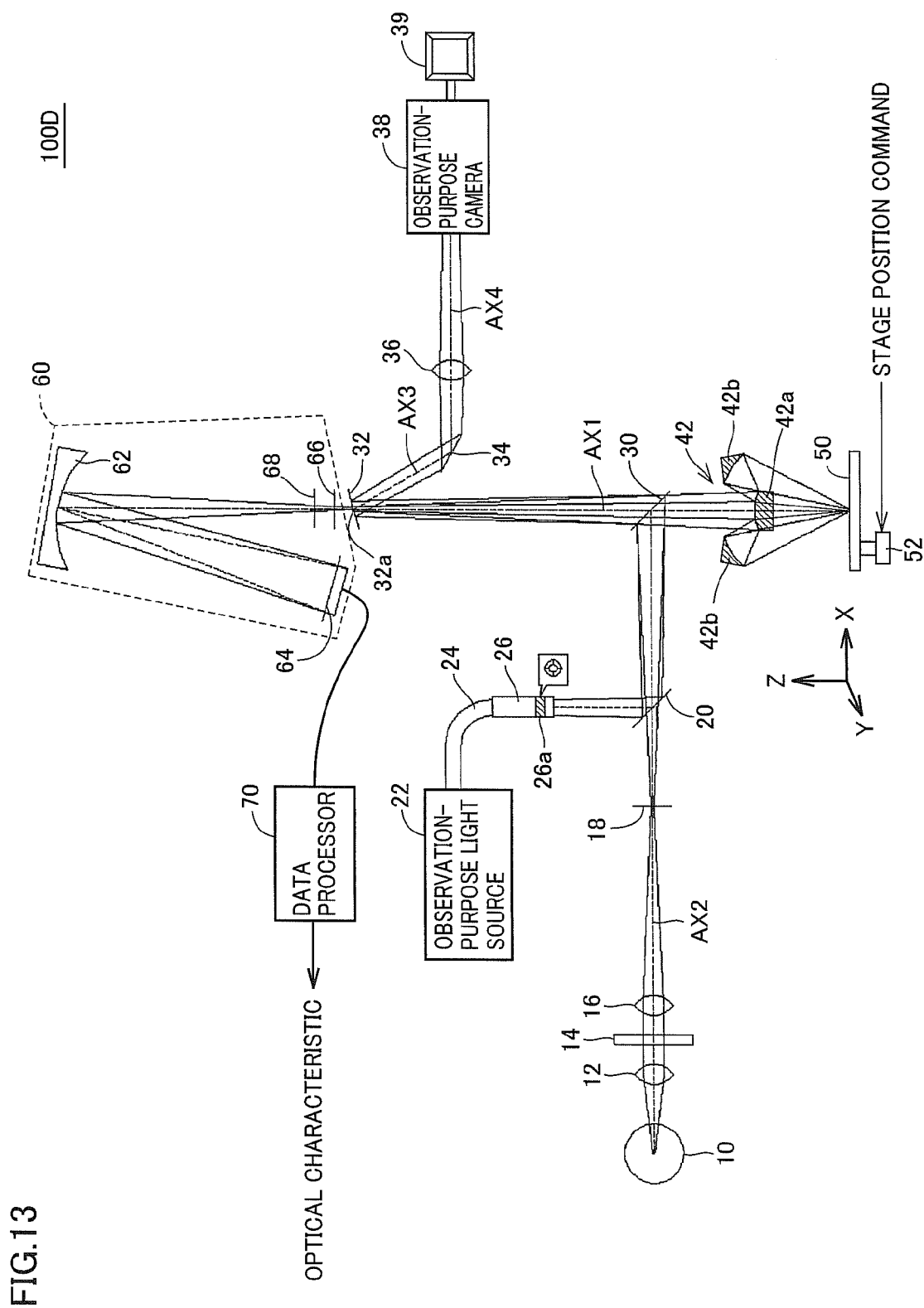
FIG. 13 is a schematic configuration diagram of an optical characteristic measuring apparatus according to a fourth embodiment of the present invention.

FIG. 13 is a schematic configuration diagram of an optical characteristic measuring apparatus 100D according to a fourth embodiment of the present invention.

Referring to FIG. 13, optical characteristic measuring apparatus 100D in the fourth embodiment of the present invention differs from optical characteristic measuring apparatus 100B shown in FIG. 5 in that the position of beam splitter 20 is changed to a position on an optical path from measurement-purpose light source 10 to beam splitter 30, and respective positions of observation-purpose light source 22, optical fiber 24 and emitting portion 26 are changed according to the positional change of the beam splitter. Other functions and elements are similar to those of optical characteristic measuring apparatus 100B shown in FIG. 5, and the detailed description thereof will not be repeated. Further, as described above in connection with the third embodiment, the number of beam splitters through which the reflected light passes can be decreased to reduce the amount of attenuation of the reflected light entering spectroscopic measuring portion 60. Therefore, the SN ratio of the spectrum detected by spectroscopic measuring portion 60 can be kept higher.

According to the fourth embodiment of the invention, the effect that the precision in measurement can be further improved is achieved in addition to the effect obtained by the above-described second embodiment.

Although the present invention has been described and illustrated in detail, it is clearly understood that the same is by way of illustration and example only and is not to be taken by way of limitation, the scope of the present invention being interpreted by the terms of the appended claims.

What is claimed is:

1. An optical characteristic measuring apparatus comprising:
    a measurement-purpose light source generating a measurement light including a component in a wavelength range for measurement of an object to be measured;
    an observation-purpose light source generating an observation light including a component that can be reflected from said object;
    a condensing optical system to which said measurement light and said observation light are applied and which condenses the applied light;
    a light injecting portion, at a predetermined position on an optical path from said measurement-purpose light source to said condensing optical system, injecting said observation light;
    a light separating portion separating a reflected light generated at said object into a measurement reflected light and an observation reflected light;
    an output portion outputting at least one of a reflected image obtained from said observation reflected light and a signal according to the reflected image;
    an adjusting mechanism capable of changing a positional relation between said condensing optical system and said object; and
    a mask portion masking a part of said observation light such that a predetermined observation reference image is projected on said object to be measured, wherein said observation reference image is a pattern for adjusting a focus of an object to be measured that includes an unblocked region of which a light intensity substantially corresponds to that of an observation light, and a shadow region of which the light intensity is substantially zero.

2. The optical characteristic measuring apparatus according to claim 1, wherein
    said measurement light at said light injecting portion has a beam diameter smaller than a beam diameter of said observation light at said light injecting portion.

3. The optical characteristic measuring apparatus according to claim 1, further comprising a spectroscopic measuring portion measuring a spectrum of said measurement reflected light, wherein
    said light separating portion includes a light reflecting portion disposed on a path where the reflected light generated at said object propagates,
    said light reflecting portion includes an opening having a diameter smaller than a beam diameter of said measurement reflected light, said opening being located at a position corresponding to a light axis of the reflected light generated at said object, and
    said spectroscopic measuring portion is positioned to receive the reflected light having passed through said opening.

4. The optical characteristic measuring apparatus according to claim 1, wherein
    said condensing optical system includes a convex reflecting mirror and a concave reflecting mirror,
    said convex reflecting mirror directs to said concave reflecting mirror a light entering a region located at least a predetermined radius from a light axis of said measurement light in a cross section orthogonal to the light axis of said measurement light, and
    said concave reflecting mirror concentrates the light from said convex reflecting mirror on said object.

5. The optical characteristic measuring apparatus according to claim 1, wherein
    said output portion includes a display showing said reflected image.

6. The optical characteristic measuring apparatus according to claim 1, wherein
    said observation-purpose light source stops generating said observation light in a period in which measurement is performed using said measurement reflected light.

7. The optical characteristic measuring apparatus according to claim 1, wherein the mask portion is disposed on a path from the observation-purpose light source to the light injection portion.

8. The optical characteristic measuring apparatus according to claim 1, wherein the mask portion is configured to mask only the observation light.

9. A method of measuring an optical characteristic of an object to be measured, using an optical characteristic measuring apparatus,
    said optical characteristic measuring apparatus including:
        a measurement-purpose light source generating a measurement light including a component in a wavelength range for measurement of said object;
        an observation-purpose light source generating an observation light including a component that can be reflected from said object;

a condensing optical system to which said measurement light and said observation light are applied and which condenses the applied light;

a light injecting portion, at a predetermined position on an optical path from said measurement-purpose light source to said condensing optical system, injecting said observation light;

a light separating portion separating a reflected light generated at said object into a measurement reflected light and an observation reflected light;

an adjusting mechanism capable of changing a positional relation between said condensing optical system and said object; and a mask portion masking a part of said observation light such that a predetermined observation reference image is projected on said object to be measured, wherein said observation reference image is a pattern for adjusting a focus of an object to be measured that includes an unblocked region of which a light intensity substantially corresponds to that of an observation light, and a shadow region of which the light intensity is substantially zero, and said method comprising the steps of:

generating said observation light by said observation-purpose light source;

masking said part of said observation light such that said predetermined observation reference image is projected on said object to be measured;

obtaining a reflected image from said observation reflected light separated by said light separating portion;

driving said adjusting mechanism based on a state of focusing shown by said reflected image;

generating said measurement light by said measurement-purpose light source; and measuring a spectrum of said measurement reflected light separated by said light separating portion.

10. The method of measuring an optical characteristic according to claim 9, further comprising the step of stopping generation of said observation light by said observation-purpose light source, when generation of said measurement light is started.

11. The method of measuring an optical characteristic according to claim 9, wherein the mask portion is disposed on a path from the observation-purpose light source to the light injection portion.

12. The method of measuring an optical characteristic according to claim 9, wherein the mask portion is configured to mask only the observation light.

13. An optical characteristic measuring apparatus comprising:

a measurement-purpose light source generating a measurement light including a component in a wavelength range for measurement of an object to be measured;

an observation-purpose light source generating an observation light including a component that can be reflected from said object;

a condensing optical system to which said measurement light and said observation light are applied and which condenses the applied light;

a light separating portion separating a reflected light generated at said object into a measurement reflected light and an observation reflected light;

an output portion outputting at least one of a reflected image obtained from said observation reflected light and a signal according to the reflected image;

an adjusting mechanism capable of changing a positional relation between said condensing optical system and said object;

a first light injecting portion, at a first position between said measurement-purpose light source and said condensing optical system on a light axis of the reflected light, injecting said observation light;

a second light injecting portion, at a second position between said first light injection portion and said condensing optical system on the light axis of the reflected light, injecting said measurement light; and a mask portion masking a part of said observation light such that a predetermined observation reference image is projected on said object to be measured, wherein said observation reference image is a pattern for adjusting a focus of an object to be measured that includes an unblocked region of which a light intensity substantially corresponds to that of an observation light, and a shadow region of which the light intensity is substantially zero.

* * * * *